United States Patent
Varma et al.

(10) Patent No.: US 7,879,270 B2
(45) Date of Patent: Feb. 1, 2011

(54) PROCESS FOR PRODUCING A HYPER-ELASTIC, HIGH STRENGTH DILATATION BALLOON MADE FROM MULTI-BLOCK COPOLYMERS

(75) Inventors: Ashish Varma, Galway (IE); Kimberly A. Chaffin, Plymouth, MN (US); Frank Bates, St. Louis, MN (US); Marc Hillmyer, Minneapolis, MN (US); Lisa Lim, Minneapolis, MN (US)

(73) Assignees: Medtronic, Inc, Minneapolis, MN (US); Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 12/869,273

(22) Filed: Aug. 26, 2010

(65) Prior Publication Data

US 2010/0320634 A1 Dec. 23, 2010

Related U.S. Application Data

(60) Continuation of application No. 12/261,090, filed on Oct. 30, 2008, now abandoned, which is a division of application No. 10/920,458, filed on Aug. 18, 2004, now abandoned.

(60) Provisional application No. 60/495,711, filed on Aug. 18, 2003.

(51) Int. Cl.
B29C 47/00 (2006.01)

(52) U.S. Cl. ............... 264/176.1; 264/108; 264/209.5; 264/514; 264/532; 264/573; 604/915

(58) Field of Classification Search ............... 264/108, 264/176.1, 209.1–209.5, 235, 346, 500, 512, 264/514, 523, 529–532, 535, 540, 573; 428/35.7, 428/36.9, 36.91, 36.92; 524/494, 543; 604/96.01, 604/101.02, 103.11, 915; 606/191, 192, 606/194

See application file for complete search history.

(56) References Cited

U.S. PATENT DOCUMENTS

| | | | |
|---|---|---|---|
| 3,993,534 A | 11/1976 | Nagatuma et al. |
| 4,041,103 A | 8/1977 | Davison et al. |
| 4,053,442 A | 10/1977 | Jungr et al. |

(Continued)

FOREIGN PATENT DOCUMENTS

EP 374961 6/1990

(Continued)

OTHER PUBLICATIONS

U.S. Appl. No. 12/261,090 Non Final Office Action dated Sep. 18, 2009.

(Continued)

*Primary Examiner*—Joseph S Del Sole
*Assistant Examiner*—Dimple Bodawala (57) ABSTRACT

A process for producing a dilatation balloon by extruding a multiblock copolymer composition to form an extrudate comprising phase-separated glassy, rubber, and semicrystalline microdomains that are macroscopically ordered in a perpendicular alignment. The balloon formed by the process demonstrates, during inflation, a true stress vs. nominal strain response curve comprising a first zone representative of a low modulus balloon, a second zone representative of a high strength balloon, and a sharp transition from the first zone to the second zone.

23 Claims, 8 Drawing Sheets

U.S. PATENT DOCUMENTS

| | | | |
|---|---|---|---|
| 4,173,612 A | 11/1979 | Kelly | |
| 4,762,657 A | 8/1988 | Rogers et al. | |
| 5,102,402 A | 4/1992 | Dror et al. | |
| 5,156,785 A | 10/1992 | Zhraahala | |
| 5,290,306 A | 3/1994 | Trotta et al. | |
| 5,304,340 A | 4/1994 | Downey | |
| 5,306,246 A * | 4/1994 | Sahatjian et al. | 604/96.01 |
| 5,348,538 A | 9/1994 | Wang et al. | |
| 5,412,068 A | 5/1995 | Tang et al. | |
| 5,486,593 A | 1/1996 | Tang et al. | |
| 5,500,180 A * | 3/1996 | Anderson et al. | 264/532 |
| 5,556,383 A | 9/1996 | Wang et al. | |
| 5,707,354 A | 1/1998 | Salmon et al. | |
| 5,783,633 A * | 7/1998 | Sperling et al. | 525/131 |
| 5,834,583 A | 11/1998 | Hancock et al. | |
| 5,879,369 A | 3/1999 | Ishida | |
| 6,045,877 A | 4/2000 | Gleason et al. | |
| 6,093,463 A | 7/2000 | Thakrar | |
| 6,171,278 B1 | 1/2001 | Wang et al. | |
| 6,200,290 B1 | 3/2001 | Burgmeier | |
| 6,210,364 B1 * | 4/2001 | Anderson et al. | 604/96.01 |
| 6,283,939 B1 | 9/2001 | Anderson et al. | |
| 6,287,314 B1 | 9/2001 | Lee et al. | |
| 6,306,973 B1 | 10/2001 | Takaoka et al. | |
| 6,328,710 B1 | 12/2001 | Wang et al. | |
| 6,350,820 B1 | 2/2002 | Hahnfeld et al. | |
| 6,376,621 B1 | 4/2002 | Hahnfeld et al. | |
| 6,426,390 B1 | 7/2002 | Hahnfeld et al. | |
| 6,451,924 B1 | 9/2002 | Hahnfeld et al. | |
| 6,455,656 B2 | 9/2002 | Hahnfeld et al. | |
| 6,495,090 B1 | 12/2002 | Wilkins | |
| 6,645,422 B2 | 11/2003 | Jung et al. | |
| 6,787,095 B2 | 9/2004 | Wang et al. | |
| 6,863,856 B1 | 3/2005 | Mahoney et al. | |
| 6,863,861 B1 | 3/2005 | Zhang et al. | |
| 6,914,091 B2 | 7/2005 | Donald et al. | |
| 6,977,103 B2 | 12/2005 | Chen et al. | |
| 7,078,091 B2 | 7/2006 | Bonk et al. | |
| 7,084,209 B2 | 8/2006 | Everaerts et al. | |
| 7,465,164 B2 * | 12/2008 | Holman et al. | 425/526 |
| 7,618,696 B2 * | 11/2009 | Wang et al. | 428/36.92 |
| 7,700,033 B2 * | 4/2010 | Wang et al. | 264/540 |
| 7,723,422 B2 * | 5/2010 | Zoromski et al. | 524/494 |
| 2002/0010420 A1 | 1/2002 | Bagaoisan et al. | |
| 2002/0041940 A1 | 4/2002 | Jung, Jr. et al. | |
| 2002/0053349 A1 * | 5/2002 | Anderson et al. | 128/898 |
| 2002/0132072 A1 | 9/2002 | Wang et al. | |
| 2003/0144418 A1 | 7/2003 | Donald et al. | |
| 2003/0167067 A1 * | 9/2003 | Wang et al. | 606/192 |
| 2004/0028611 A1 | 2/2004 | Wox | |
| 2004/0173935 A1 * | 9/2004 | Lim et al. | 264/209.3 |
| 2004/0213933 A1 | 10/2004 | Varma | |
| 2005/0043808 A1 | 2/2005 | Felt et al. | |
| 2005/0118370 A1 | 6/2005 | Varma et al. | |
| 2005/0149172 A1 | 7/2005 | Varma | |
| 2005/0181004 A1 | 8/2005 | Hunter et al. | |
| 2005/0184619 A1 | 8/2005 | Chen | |
| 2007/0138694 A1 | 6/2007 | Sridharan | |
| 2007/0197961 A1 | 8/2007 | Wang et al. | |
| 2007/0238835 A1 | 10/2007 | Chen | |

FOREIGN PATENT DOCUMENTS

| | | |
|---|---|---|
| EP | 531117 A2 * | 3/1993 |
| EP | 0592885 | 4/1994 |
| EP | 1743644 | 10/2000 |
| WO | WO95/23619 | 9/1995 |
| WO | WO99/44649 | 9/1999 |
| WO | WO0145784 | 6/2001 |

OTHER PUBLICATIONS

U.S. Appl. No. 10/920,457, Non Final Office Action dated Jan. 15, 2010.

Bates et al., "Block Copolymers—Designer Soft Materials" Physics Today, 52:32-38 (Feb. 1999).

Cochran et al., "Thermodynamic Behavior of Poly (Cyclohexylethylene) in Polyolefin Diblock Copolymers" AIChE, Aug. 2002; pp. 1-7.

Eseanult et al. "Development of Elastomers Based on Fully Hydrogenated Styrene-Diene" Dow Chemical Co. Corporate R and D, Midland, MI; J. Wiley 7 Sons; ISBM:0-470-84335-7.

McGraw-Hill Dictionary of Scientific and Technical Terms, pp. 433, 1989.

McGraw-Hill Dictionary of Scientific and Technical Terms, pp. 230, 1989.

Ruokolainen et al., Effect of Thermal History and Microdomain Orientation Macromolecules, 2002; 35:9391-9402.

Harada et al., "Transverse Orientation of Lamellae and Cylinders by Solution Extrusion of a Pentablock Copolymer" published on Jun. 28, 2003, American Chemical Society (AIChE), macromolecules 2003, vol. 36, p. # 5440-5442.

Hermel et al., "Shear-Induced Lamellae Alignment in Matched Triblock and Pentablock Copolymers" published on May 10, 2002, AIChE, macromolecules 2002, vol. 35, p. 468CX5-4689.

Ryu et al., "Chain Architecture Effects on Deformation and Fracture of Block Copolymers with Unentangles Mtrics" published on Feb. 13, 2002, AIChE, macromolecules, vol. 35, pp. 2157-2166.

"Pellethane 2363-75D Technical Data Sheet" Lubrizol Advanced Materials, inc., Cleveland, OH Jun. 4, 2007, 1pg.

Sperling "11.2.2 Cold Drawing in Crystalline Polymers," Introduction to Physical Polymer Science, New York, NY, 1992, pp. 513-151.

* cited by examiner

PROCESS FOR PRODUCING A HYPER-ELASTIC, HIGH STRENGTH DILATATION BALLOON MADE FROM MULTI-BLOCK COPOLYMERS

CROSS-REFERENCE TO RELATED APPLICATIONS

The present application is a continuation of U.S. patent application Ser. No. 12/261,090, filed Oct. 30, 2008, which is a divisional application of U.S. patent application Ser. No. 10/920,458, filed Aug. 18, 2004, now abandoned, which claims the benefit of U.S. Provisional Patent Application No. 60/495,711, filed Aug. 18, 2003, all of which are incorporated herein in their entirety for all purposes.

BACKGROUND OF THE INVENTION

1. Field of the Invention

The present invention relates to the field of balloon dilatation. Specifically, the present invention relates to balloons for dilatation applications and a process for manufacturing the balloons.

2. Related Art

Surgical procedures employing balloons and medical devices incorporating those balloons (i.e. balloon catheters) are becoming more common and routine. These procedures, such as angioplasty procedures, are conducted when it becomes necessary to expand or open narrow or obstructed openings in blood vessels and other passageways in the body to increase the flow through the obstructed areas. For example, in the technique of Percutaneous Transluminal Coronary Angioplasty (PTCA), a dilatation balloon catheter is used to enlarge or open an occluded blood vessel which is partially restricted or obstructed due to the existence of a hardened stenosis or buildup within the vessel. This procedure requires that a balloon catheter be inserted into the patient's body and positioned within the vessel so that the balloon, when inflated, will dilate the site of the obstruction or stenosis so that the obstruction or stenosis is minimized, thereby resulting in increased blood flow through the vessel. Often, however, a stenosis requires treatment with multiple balloon inflations. Additionally, many times there are multiple stenoses within the same vessel or artery. Such conditions require that either the same dilatation balloon must be subjected to repeated inflations, or that multiple dilatation balloons must be used to treat an individual stenosis or the multiple stenoses within the same vessel or artery. Additionally, balloons and medical devices incorporating those balloons may also be used to administer drugs to patients.

Balloon catheters traditionally comprise a dilatation balloon at their distal end. Angioplasty balloons are currently produced by a combination of extrusion and stretch blow molding. The extrusion process is used to produce the balloon tubing, which essentially serves as a pre-form. This tubing is subsequently transferred to a stretch blow-molding machine capable of axially elongating the extruded tubing. U.S. Pat. No. 6,328,710 B1 to Wang et al., discloses such a process, in which tubing pre-form is extruded and blown to form a balloon. U.S. Pat. No. 6,210,364 B1; U.S. Pat. No. 6,283,939 B1 and U.S. Pat. No. 5,500,180, all to Anderson et al., disclose a process of blow-molding a balloon, in which a polymeric extrudate is simultaneously stretched in both radial and axial directions. Dilatation balloons are subsequently attached to a catheter shaft and wrapped down tightly on this shaft in order to achieve a low profile at the distal end of the catheter. The low profile serves to enhance the ability of a dilatation catheter to navigate narrow lesions.

The basic design of dilatation balloons has remained, essentially, unchanged since conception. The materials used in balloons for dilatation are primarily thermoplastics and thermoplastic elastomers such as polyesters and their block co-polymers, polyamides and their block co-polymers and polyurethane block co-polymers. U.S. Pat. No. 5,290,306 to Trotta et al., discloses balloons made from polyesterether and polyetheresteramide copolymers. U.S. Pat. No. 6,171,278 to Wang et al., discloses balloons made from polyether-polyamide copolymers. U.S. Pat. No. 6,210,364 B1; U.S. Pat. No. 6,283,939 B1 and U.S. Pat. No. 5,500,180, all to Anderson et al., disclose balloons made from polyurethane block copolymers.

Traditionally, the balloons available to physicians were classified as either "compliant" or "noncompliant." This classification is based upon the operating characteristics of the individual balloon, which in turn depended upon the process used in forming the balloon, as well as the material used in the balloon forming process. Both types of balloons provide advantageous qualities, which were not available from the other.

A balloon that is classified as "noncompliant" is characterized by the balloon's inability to grow or expand appreciably beyond its rated or nominal diameter. "Noncompliant" balloons are referred to as having minimal distensibility. In balloons currently known in the art (e.g., polyamide block copolymers), this minimal distensibility results from the strength and rigidity of the molecular chains which make up the base polymer, as well as the orientation and structure of those chains resulting from the balloon formation process. The strength resulting from this highly oriented structure is so great that when the balloon is subjected to typical inflation or operating pressures (i.e., about 70 psi to over 200 psi), it will not be stressed beyond the failure point of the polymeric material.

A balloon, which is referred to as being "compliant", is characterized by the balloon's ability to grow or expand beyond its nominal or rated diameter. In balloons previously known in the art (e.g., polyethylene, polyvinylchloride), the balloon's "compliant" nature or distensibility results from the chemical structure of the polymeric material used in the formation of the balloon, as well as the balloon forming process. These polymeric materials have a relatively low yield point. Thus, the inflation pressures used in dilation procedures are typically above the yield point of the materials used to form distensible balloons. A distensible or "compliant" balloon when inflated to normal operating pressures, which are greater than the polymer material's yield point, is subjected to stress sufficient to permanently realign the individual molecular chains of the polymeric material. The realignment of the individual polymer chains permits the balloon to expand beyond its nominal or rated diameter. However, since this realignment is permanent, the balloon will not follow its original stress-strain curve on the subsequent inflation-deflation cycles. Therefore, the balloon, upon subsequent inflations, will achieve diameters that are greater than the diameters that were originally obtained at any given pressure during the course of the balloon's initial inflation.

The yield point of a material is defined as the stress at which the individual molecular chains move in relation to one another such that when the pressure or stress is relieved there is permanent deformation of the structure. The modulus of a material, also known as the Young's modulus, is the stress per unit strain. A material, which exhibits the ability to follow the same stress-strain curve during the repeated application and relief of stress, is defined as being elastic and as having a high degree of elastic stress response.

Despite the use of high strength engineering polymers, access to highly occluded vessels and lesions in small vessels is still limited. Dilatation balloons currently available do not have a proper balance of competing properties. Balloons are needed that have low profile and are highly elastic, but also have high strengths and have high trackability to maneuver through tortuous vessels. While balloons made from polyethylene terephthalate (PET) can have lower profile than other balloons, such as polyamide copolymer balloons, the PET balloon is stiff, has a higher modulus, and therefore has inferior trackability. While balloons made from polyamide copolymers have better trackability than PET balloons due to their lower modulus, they have higher profiles thus limiting their application.

Furthermore, in attempting to produce low profile balloons by wrapping the balloon, the wrapping process often serves to reduce the burst strength of the balloon. An additional disadvantage is that dilatation balloons are not highly elastic. The initial low profile is only applicable to the first lesion that is dilated, as the balloon does not re-wrap tightly upon deflation. In the event that a patient has multiple lesions, a new catheter is used for each lesion thus adding to the cost and time of the procedure.

New dilatation balloon materials are needed that have the proper balance of these competing properties. Also, new processes are needed to produce dilatation balloons with the balanced properties. Dilatation balloons are needed that have low profile, high hoop strength, high-elasticity, high elastic recovery and high trackability.

SUMMARY OF THE INVENTION

It has been found that utilizing multiblock copolymers in solution or solutionless extrusion processes allows for the production of dilatation balloons with low profile, high hoop strength, high-elasticity, high elastic recovery and high trackability. The unique mechanical response of the balloons is due to the macroscopically aligned microdomains in the multiblock copolymers, formed during the extrusion and balloon forming process.

In an embodiment, therefore, the present invention relates to a zero-fold dilatation balloon comprising a multiblock copolymer having elasticity at nominal strains equal to or greater than about 30% 40%, 50%, 60%, 70%, 80%, 90% or 100%, where nominal strain is [(balloon o.d. at nominal pressure−preform o.d.)/preform o.d.]×100, where o.d. is outer diameter.

In another embodiment, the present invention relates to a zero-fold dilatation balloon comprising a multiblock copolymer having high elasticity and elastic recovery from nominal strains equal to or greater than about 30% 40%, 50%, 60%, 70%, 80%, 90% or 100%.

In another embodiment, the present invention relates to a self-wrapping dilatation balloon comprising a multiblock copolymer having high elasticity and elastic recovery from nominal strains equal to or greater than about 30%, 40%, 50%, 60%, 70%, 80%, 90% or 100%.

Dilatation balloons of the present invention can be used in a wide range of applications for angioplasty, stent delivery and other applications, including, but not limited to cardiovascular, neurovascular and peripheral applications.

Dilatation balloons of the present invention for use in cardiovascular applications, for example, encompass a range of balloon sizes, including but not limited to balloons having outer diameter at nominal pressures of about 0.5 mm to about 6.0 mm. One example is a 3 mm balloon. The term "3 mm balloon" is used herein to refer to dilatation balloons with an outer diameter at nominal pressures of about 3 mm. The 3 mm balloons of the present invention exemplify and illustrate the unique mechanical response of the dilatation balloons of the present invention. For example, the 3 mm balloons have hoop strengths of at least 14,000 p.s.i., elastic recovery from nominal strains greater than about 30% and high elasticities. The 3 mm balloon has a non-linear compliance curve having initial, secondary and final segments, the initial segment having a radial growth higher than the secondary segment, and the secondary segment having a radial growth higher than the final segment. The radial growth for the 3 mm balloon in mm/p.s.i. is about 0.39 for the initial segment, 0.025 for the secondary segment, and 0.017 for the final segment.

In another embodiment, the present invention relates to a polymeric extrudate for making a dilatation balloon comprising a multiblock copolymer having tensile strength in the range of about 50 MPa to about 450 MPa, strain at break in the range of about 50% to about 600% and elasticity at nominal strains of at least about 30%.

In another embodiment, the present invention relates to a polymeric extrudate for making a dilatation balloon comprising a multiblock copolymer having tensile strength in the range of about 50 MPa to about 450 MPa, strain at break in the range of about 50% to about 600% and substantially complete elastic recovery from strains of at least about 30%. One particular, non-limiting example is an extrudate for making a 3 mm balloon having tensile strength in the range of about 150 MPa to about 250 MPa, strain at break in the range of about 300% to about 500% and substantially complete elastic recovery from strains of at least about 30%. An alternative example is an extrudate having tensile strength in the range of about 50 MPa to about 150 MPa, strain at break in the range of about 50% to about 300% and substantially complete elastic recovery from strains of at least about 30%. Another example is an extrudate having tensile strength in the range of about 250 MPa to about 450 MPa, strain at break in the range of about 500% to about 600% and substantially complete elastic recovery from nominal strains of at least about 30%.

Extrudates of the present invention can have a tubular shape. Extrudates can have outer diameter of about 0.025 mm to about 13 mm and inner diameter of about 0.013 mm to about 12 mm. In one particular example, an extrudate for a 3 mm balloon, can have a tubular shape with an outer diameter of about 0.25 mm to about 2.5 mm and an inner diameter of about 0.15 mm to about 1.5 mm. The extrudates of the present invention, including, but not limited to the extrudate for the 3 mm balloon, have phase-separated microdomains that are macroscopically aligned in parallel, perpendicular, transverse, or a combination thereof. Alternatively, the extrudate can have two or more regions with different macroscopic microdomain alignment.

In another embodiment, the present invention relates to a process for producing a polymeric extrudate for use as a dilatation balloon. The process comprises contacting a multiblock copolymer with a solvent to form a multiblock copolymer mixture, extruding the multiblock copolymer mixture to form an extrudate, and drawing the extrudate, wherein the extrudate has tensile strength in the range of about 50 MPa to about 450 MPa, strain at break in the range of about 50% to about 600% and elasticity at nominal strains of at least about 30%. Optionally, the extrudate has substantially complete elastic recovery from nominal strains of at least about 30%.

In another embodiment, the present invention relates to an alternative process for producing a polymeric extrudate for use as a dilatation balloon. The process comprises extruding a multiblock copolymer composition to form an extrudate, and drawing the extrudate, wherein the extrudate has tensile strength in the range of about 50 MPa to about 450 MPa, strain at break in the range of about 50% to about 600% and elasticity at nominal strains of at least about 30%.

In the process, the extruding is done at a constant rate such that the extrudate has phase-separated microdomains that are macroscopically aligned in parallel, perpendicular, transverse, or a combination thereof. Alternatively, the extruding is done at a variable rate such that the extrudate has two or more regions with different macroscopic microdomain alignment. The temperature of the extrusion is equal to or less than the order-disorder transition temperature for the multiblock copolymer. After extrusion, the process optionally comprises the step of coagulating the extrudate.

Additional features and advantages of the invention will be set forth in the description that follows, and in part will be apparent from the description, or may be learned by practice of the invention. The advantages of the invention will be realized and attained by the structure and particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE FIGURES

The accompanying drawings, which are included to illustrate exemplary embodiments of the invention and are incorporated in and constitute a part of this specification, illustrate embodiments of the invention and together with the description serve to explain the principles of the invention. In the drawings.

The present invention will now be described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE INVENTION

Reference will now be made in detail to the embodiments of the present invention, examples of which are illustrated in the accompanying drawings.

Preform is used herein to refer to the drawn, uniaxially or biaxially, tubular extrudate formed upon extruding and drawing the multiblock copolymer mixture or composition. The preform is used in the process of producing a dilatation balloon. The process of forming dilatation balloons from tubular preforms are well known to one of skill in the relevant art. The preform can be a drawn extrudate, formed upon drawing the extrudate in, for example, a balloon forming machine. Extrudate is used herein to refer to the article formed by extruding the multiblock copolymer mixture or composition. The extrudate can be used in forming a dilatation balloon preform, or optionally, can be used in forming another article, for example, a tubular extrudate for use in another medical application.

The terms "microdomain" and "microphase" are used generally to refer to the domains and phases in the multiblock copolymers. The terms "microdomain" and "microphase" should not be construed to be limiting in the size of the domain or phase. The terms "microdomain" and "microphase" are understood to include, but are not limited to nanometer-sized domains and phases such as nanodomains and nanophases, micrometer-sized domains and phases such as microdomains and microphases, and other sized domains and phases.

The term "dilatation balloon" refers generally to the types of balloons included in the present invention. Dilatation balloon, for example, includes, but is not limited to angioplasty balloons, stent delivery balloons and others. It should be understood that the term "dilatation balloon" is referred to throughout the description herein for illustrative purposes, and it is intended that the descriptions herein encompass different balloon sizes depending on the application. Although specific examples of balloons for particular applications are described for exemplary purposes, it should be understood that the scope of the invention is not limited to the exemplified balloons. While the balloons of the present invention can vary in size, and can be used for different applications, they all exhibit the unique mechanical response described herein, namely, they exhibit low profile, high hoop strength, high-elasticity, high elastic recovery and high trackability.

One embodiment of the present invention relates to a zero-fold dilatation balloon comprising a multiblock copolymer having high hoop strength, high elasticity and high elastic recovery.

Another embodiment of the present invention relates to a self-wrapping dilatation balloon comprising a multiblock copolymer having high hoop strength, high elasticity and high elastic recovery.

Figure 1:
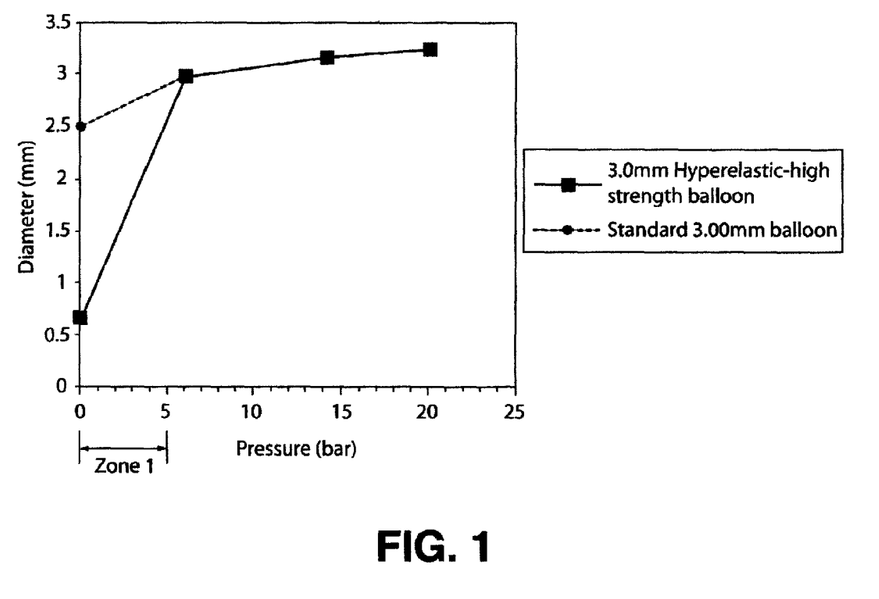
FIG. 1 shows idealized (prophetic) compliance curves for the dilatation balloons of the present invention as compared to a standard 3.00 mm balloon.

The balloons of the present invention are formed from multiblock copolymers and exhibit high elasticity. For example, the 3 mm balloon exhibits high elasticity over an initial low-inflation pressure range. FIG. 1 shows an example of an idealized or prophetic compliance curve for 3 mm balloons of the present invention compared to conventional 3 mm balloons. In zone 1 of FIG. 1, the high elasticity zone, 3 mm balloons of the present invention have a growth rate of about 0.39 mm/p.s.i., compared to about 0.08 mm/p.s.i. for the conventional balloons. The hyper-elastic characteristics of the balloons of the present invention allow for zero-fold and self-wrapping characteristics. Other sized balloons of the present invention exhibit similar, highly elastic responses.

Figure 2:
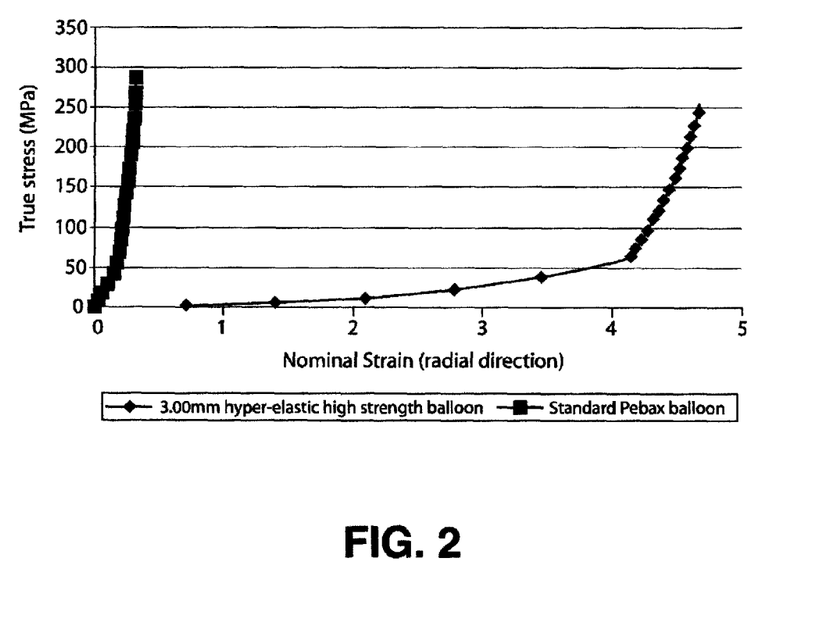
FIG. 2 shows the idealized (prophetic) true stress vs. nominal strain curves for a cylindrical dilatation balloon of the present invention as compared to a standard polyamide copolymer balloon, both during inflation.

FIG. 2 shows the corresponding true stress vs. nominal strain response for both 3 mm balloon inflations shown in FIG. 1. The idealized or prophetic response curve highlights, for 3 mm dilatation balloons of the present invention, the initial high elasticity zone and low modulus over the initial high elasticity zone. A sharp transition can be seen to the inelastic-high strength zone. Minimal hysteresis in the dilatation balloons of the present invention ensures complete elastic recovery to the initial balloon form and dimensions. The stress-strain curve for the conventional polyamide copolymer balloon shows that materials used to manufacture conventional balloons exhibit significantly less elasticity, over the initial elasticity zone, and modulus typically higher than the 3 mm dilatation balloons of the present invention.

Figures 3A, 3B:
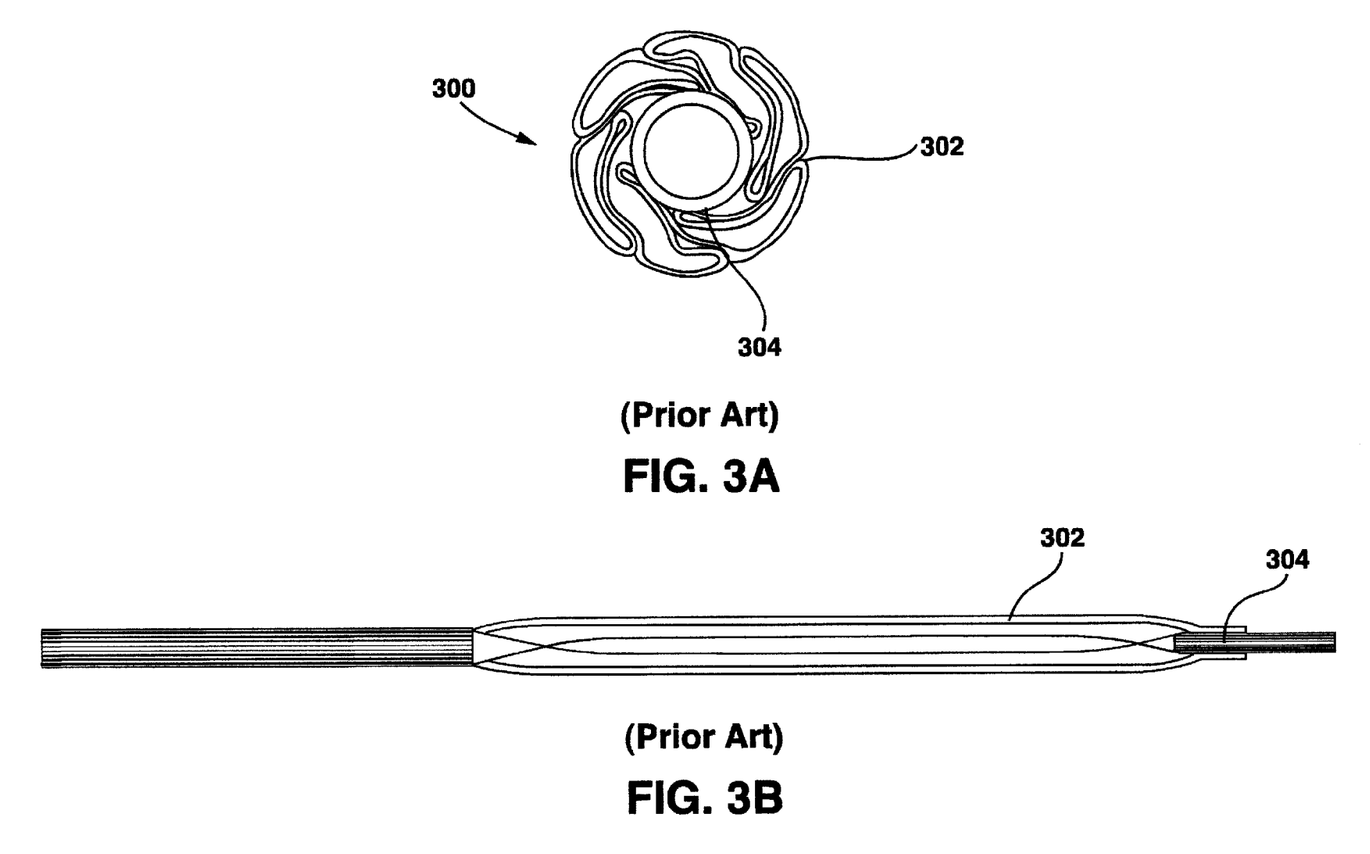
FIG. 3A illustrates a cross-sectional view of a traditional balloon wrapped around a catheter.
FIG. 3B illustrates a side-view of a traditional balloon wrapped around a catheter.

The term wrapping is well known to one of ordinary skill in the art and refers to how the dilatation balloon is disposed about a catheter to create a low profile during delivery of the balloon to the treatment site. Traditionally, a dilatation balloon is wrapped down tightly on a catheter shaft, in a separate manufacturing process, to achieve a low profile at the distal end. FIG. 3A shows a cross section of a traditional balloon catheter assembly 300 having a balloon 302 wrapped down tightly on a catheter shaft 304. FIG. 3B shows a side view of wrapped balloon 302 and catheter shaft 304. The wrapping process, however, often reduces the burst strength of the balloon. In addition, the initial low profile of the wrapped balloon is only applicable before initial inflation and to the first lesion that is dilated, because the balloon typically does not re-wrap as tightly upon deflation. The number of lesions that can be treated with a traditional wrapped balloon is limited.

Figure 4A:
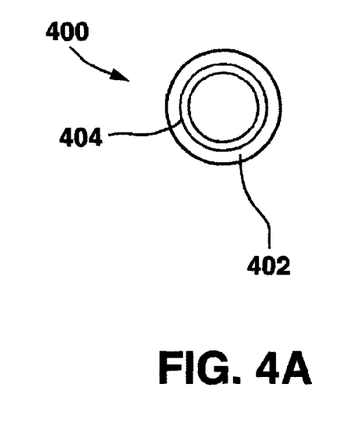
FIG. 4A illustrates a cross-sectional view of a zero-fold balloon mounted on a catheter, according to an embodiment of the present invention.
Figure 4B:
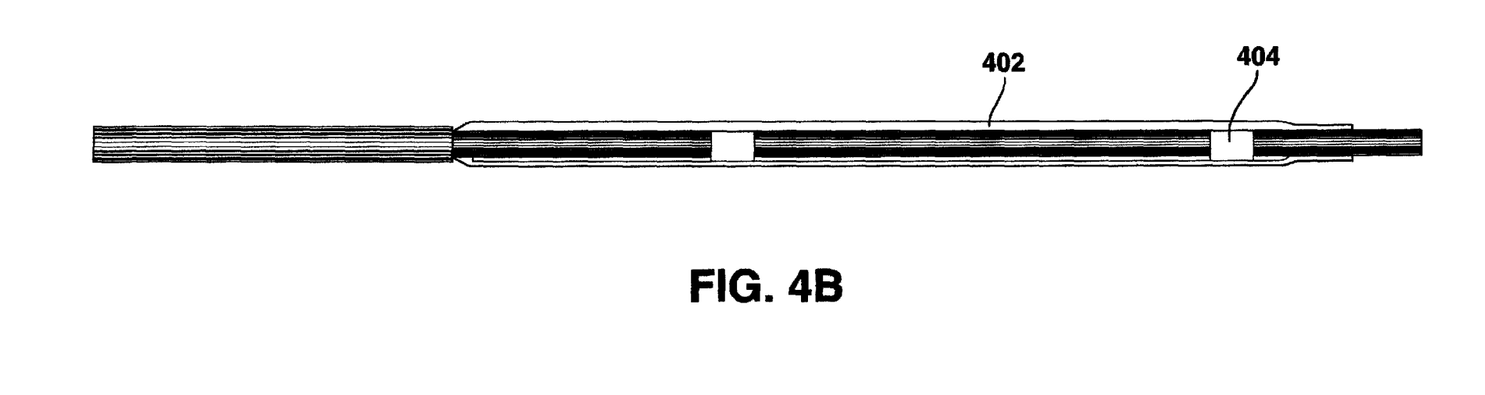
FIG. 4B illustrates a side-view of a zero-fold balloon mounted on a catheter, according to an embodiment of the present invention.

In contrast to the balloons of the prior art, the balloons of the present invention are zero-fold, have low profiles and have high elasticity. The phrase zero-fold is used herein to refer to balloons that preferably have no folds or wraps. Alternatively, balloons of the present invention have substantially no folds or wraps and have a lower profile than the balloons in the current art. For example, FIG. 4A shows a cross section of a zero-fold balloon catheter assembly 400 having a balloon 402 mounted on a catheter shaft 404. FIG. 4B shows a side view of zero-fold balloon 402 mounted on catheter shaft 404. Zero fold balloons of the present invention have high elasticity and high elastic recovery, which gives rise to self-wrapping characteristics. Self-wrapping refers to the characteristic of a highly elastic balloon where, after initial inflation and upon deflation, the balloon returns to a low profile over the catheter tubing. Preferably, the balloon returns to approximately the same low profile it had before the initial inflation.

In fact, before initial inflation and when deflated, the zero-fold balloons of the present invention have a much lower profile than wrapped conventional balloons, and can have essentially the same dimensions as the tubular pre-form. When inflated, balloons of the present invention transition from a low profile tube to a conventional balloon and revert to the initial tubular form when deflated, even after multiple inflations and after multiple lesions have been dilated. Balloons of the present invention have elasticity at nominal strains of at least about 30%. Alternatively, balloons of the present invention have elastic recovery from nominal strains equal to or greater than about 30%, 40%, 50%, 60%, 70%, 80%, 90% or 100%, where nominal strain is [(balloon o.d. at nominal pressure−preform o.d.)/preform o.d.]×100, where o.d. is outer diameter. The balloons of the present invention may, therefore, be used to dilate multiple lesions without compromising primary performance.

The low profile of the present invention allows a surgeon to use the balloon in very small arteries that may have a large degree of blockage or plaque build-up. Conventional 3.0 mm balloons at zero atmospheres have an outer diameter of about 2.5 mm when deflated and inflate to about 3.0 to about 3.3 mm when close to bursting. Balloons of the present invention can have much lower profile and maintain high hoop strength, allowing for their use in a wider range of applications. For example, 3 mm dilatation balloons of the present invention can have outer diameters of about 0.25 mm to about 2.5 mm when deflated and about 3.5 mm to about 4.0 mm outer diameter when inflated close to bursting. Alternatively, the balloons of the present invention can be produced to have lower profiles for other applications, for example, neurovascular applications. Alternatively, the balloons can be produced to have lower or larger profiles for other applications, for example peripheral applications.

Dilatation or distensibility is used herein to refer to the expandability of the balloon. Balloons of the present invention are sufficiently expandable to treat various sized arteries and for stent delivery, i.e., have radial growths about 2% to about 40% between nominal and rated pressures. Preferably, the radial growth of the balloon is in the range of about 5% to about 20%.

Balloons of the present invention have sufficient hoop strengths to dilate occluded vessels without bursting and for stent delivery or other applications. Hoop strength is directly related to the maximum amount of pressure the balloon can withstand, for a given material and a given balloon wall thickness, without failing. The balloons of the present invention have hoop strengths upon dilatation of about 12,000 to about 75,000 p.s.i. Preferably, balloons of the present invention have hoop strengths greater than 14,000 p.s.i.

The unique mechanical response of the dilatation balloons of the present invention is achieved by utilizing multiblock copolymers in either a solutionless or solution extrusion process. The multiblock copolymer is extruded to form a polymeric extrudate that is a tubular pre-form. The extrudate can be further processed using methods well known to one of ordinary skill in the art to produce the dilatation balloons of the present invention. Once formed, the balloons can be attached to the distal end of a tubular elongated catheter shaft to form a balloon dilatation catheter. The distal portion of the catheter can have a profile in the range of about 0.025 mm to about 13.0 mm when the balloon is deflated. For a 3 mm balloon, the distal portion of the catheter can have a profile in the range of about 0.25 mm to about 2.5 mm when the balloon is deflated. The distal portion of the catheter can have substantially the same profile after one or more expansions of the balloon with rated pressures that result in about 5% to about 20% radial growth of the balloon.

In another embodiment, the present invention relates to a polymeric extrudate for making a dilatation balloon comprising a multiblock copolymer. Multiblock copolymers, the corresponding polymeric extrudates and dilatation balloons for use in the invention have a Young's Modulus less than about 5 GPa.

Extrudates of the present invention have tensile strength in the range of about 50 MPa to about 450 MPa, strain at break in the range of about 50% to about 600% and elasticity at nominal strains of at least about 30%. Optionally, extrudates of the present invention also have substantially complete elastic recovery from nominal strains of at least about 30%. One particular, non-limiting example is an extrudate for making a 3 mm balloon having tensile strength in the range of about 150 MPa to about 250 MPa, strain at break in the range of about 300% to about 500% and substantially complete elastic recovery from strains of at least about 30%. An alternative example is an extrudate having tensile strength in the range of about 50 MPa to about 150 MPa, strain at break in the range of about 50% to about 300% and substantially complete elastic recovery from strains of at least about 30%. Another example is an extrudate having tensile strength in the range of about 250 MPa to about 450 MPa, strain at break in the range of about 500% to about 600% and substantially complete elastic recovery from strains of at least about 30%.

Multiblock copolymers for use in the present invention include those multiblock copolymers that microphase separate. Microphase separation is a phenomenon unique to copolymers and is well known in the art. See, e.g., Bates, F. S. and Fredrickson, G. H., *Physics Today* February, 1999, pages 32-38. Microphase separation occurs due to the incompatibility of the polymeric blocks within the multiblock copolymer. Multiblock copolymers can phase separate to form spherical, cylindrical, lamellae or other structures of one block or phase, dispersed in a different block or phase. Using techniques well known in the art, for example, reciprocal shearing, the incompatible phases can be induced to orient macroscopically, thereby inducing long-range order in separate phases. Macroscopic ordering or alignment of the separated blocks or phases can result in a variety of alignments between the phases or microdomains. The size of the microdomains can vary from about 5 nm to about 1000 nm. These alignments include, but are not limited to parallel, perpendicular and transverse alignments. The different alignments give rise to highly anisotropic mechanical responses for the resulting material. Therefore, dilatation balloons can be flexible and steerable, while having high hoop strength, high elasticity and high elastic recovery.

Any method known to one of skill in the relevant art can be used to measure the macroscopic ordering of the polymer blocks or phases, for example, X-ray crystallography or diffractometry can be used. Using X-ray diffractometry, both the type of alignment and the degree of alignment can be measured in the extrudates and the dilatation balloons of the present invention.

Examples of multiblock copolymers for use in the present invention include, but are not limited to diblock, triblock, butablock, pentablock, hexablock, heptablock, octablock, nonablock, decablock, undecablock or dodecablock copolymers. The choice of number of blocks depends on the microphase separation and mechanical response needed. As the number of blocks is increased, the level of microphase separation and the macroscopic alignment decreases with detrimental effects to the mechanical response of the dilatation balloon.

Multiblock copolymers can have two different polymer blocks, or alternatively, they can have three or more different polymer blocks. For example, a triblock copolymer can have two different polymer blocks, represented as (A-B-A), or alternatively, it can have three different polymer blocks, represented as (A-B—C). A single multiblock copolymer can be used, or alternatively, a combination or blend of two or more of the same or different multiblock copolymers can be used. For example, a dilatation balloon of the present invention can comprise 100% triblock copolymer plus other optional additives, or alternatively, it can comprise 10% pentablock copolymer and 90% triblock copolymer plus other optional additives.

The polymer blocks can have any chemical structure, so long as the multiblock copolymer microphase separates. Examples of polymer blocks for use in the invention include, but are not limited to polyalkanes optionally substituted by alkyl, halo, ester, aryl and heteroaryl, polyhaloalkanes, polyalkenes, polyalkynes, polyarylenes, polyethers, polythioethers, polyesters, polycarbonates, polyamides, polyimides, polyurethanes, polyureas, polysulfones, polyketones, polysaccharides, polyamines, polyimines, polyphosphates, polyphosphonates, polysulfonates, polysulfonamides, polyphosphazenes and polysiloxanes. Specific examples include, but are not limited to polyethylene, polypropylene, poly(cyclohexylethylene), polyisoprene, poly(1,3-butadiene), poly(vinyl chloride), poly(vinyl fluoride), poly(chloroprene), poly(methyl acrylate), poly(methyl methacrylate), poly(acrylonitrile), polystyrene or poly(4-vinylpyridine). The polymer blocks can be of any molecular weight, as long as the resulting multiblock copolymer microphase separates. The length of each polymer block affects the orientation of the microphase separation. For example, polymer blocks can range from a single repeat unit to about one million repeat units. More specifically, polymer blocks can have molecular weights of about 10 Dalton to about 10,000,000 Dalton.

Specific examples of block copolymers for use in the present invention include but are not limited to triblock and pentablock copolymers having ABA and ABABA architectures, respectively, wherein A is a glassy phase and B is a random copolymer comprising rubber and semi-crystalline phases. Specific examples of polymers include, but are not limited to poly(vinylcyclohexane) or hydrogenated poly(styrene) for the glassy phase; hydrogenated 1,2 poly(butadiene) for the rubber phase; and hydrogenated 1,4 poly(butadiene) for the semi-crystalline phase. The physical properties of the extrudate and/or the dilatation balloon can be enhanced by tailoring one or more phases of the block copolymer. A specific example of this tailoring includes, but is not limited to increasing the linearity of the semi-crystalline phase to increase its crystallinity and thereby increase the strength of the extrudate and/or dilatation balloon.

Extrudates comprising multiblock copolymers for use in producing balloons of the present invention comprise a single layer of polymeric material. Alternatively, two or more layers of polymeric extrudate and multiblock copolymers can be used to form multilayered extrudates and multilayered dilatation balloons.

The polymeric extrudate optionally comprises a solvent. Any solvent or fluid can be used. The solubility parameter of the solvent is preferably about equal to the solubility parameter of one polymer block in the multiblock copolymer. The solubility parameter is a numerical value that indicates the relative solvency behavior of a specific solvent. Solubility parameters for many solvents are well known in the art. The solvent is selected so that it reduces entanglement in one of the polymer block phases, preferably the most entangled phase. For example, dioctylphthalate is used in reducing the entanglement in a polyethylene phase of triblock co-polyethylene co-poly(cyclohexylethylene).

Optionally, the solvent comprises a plasticizer. Alternatively, the solvent is a plasticizer. Plasticizer is used herein to mean any material that can decrease the flexural modulus of a polymer. Preferably, the solubility parameter of the plasticizer is about equal to the solubility parameter of one polymer block in the multiblock copolymer. The plasticizer may influence the morphology of the multiblock copolymer and may affect the melting temperature, glass transition temperature and order-disorder transition temperature. Examples of plasticizers include, but are not limited to: small organic and inorganic molecules, oligomers and small molecular weight polymers (those having molecular weight less than about 50,000), highly-branched polymers and dendrimers. Specific examples include: monomeric carbonamides and sulfonamides, phenolic compounds, cyclic ketones, mixtures of phenols and esters, sulfonated esters or amides, N-alkylolarylsulfonamides, selected aliphatic diols, phosphite esters of alcohols, phthalate esters such as diethyl phthalate, dihexyl phthalate, dioctyl phthalate, didecyl phthalate, di(2-ethylhexy) phthalate and diisononyl phthalate; alcohols such as glycerol, ethylene glycol, diethylene glycol, triethylene glycol, oligomers of ethylene glycol; 2-ethylhexanol, isononyl alcohol and isodecyl alcohol, sorbitol and mannitol; ethers such as oligomers of polyethylene glycol, including PEG-500, PEG-1000 and PEG-2000; and amines such as triethanol amine.

The extrudate optionally further comprises an additive or modifier. Additive and modifier are used herein to refer to any material added to the polymer to affect the polymer's properties. Examples of additives and modifiers for use in the invention include fillers, antioxidants, colorants, crosslinking agents, impact strength modifiers, viscosity modifiers, drugs and biologically active compounds and molecules. Specific examples include, but are not limited to the following. A cross-linking agent, such as diallyl phthalate, can be used to increase the mechanical strength of the extrudate and the resulting dilatation balloon. In another example, the additive comprises a polymer. For example, a multiblock copolymer mixture or composition comprising a pentablock copolymer can optionally further comprise a triblock copolymer to facilitate processing and modify the viscosity. In another example, a multiblock copolymer mixture or composition can comprise a homopolymer such as a polyethylene or a polysiloxane to facilitate processing and modify the viscosity. Polysiloxanes for use in the present invention as additives or modifiers can include any polysiloxane, for example, a polydialkylsiloxane or polydiarylsiloxane, including but not limited to polydimethylsiloxane, polydiethylsiloxane, and polydiphenylsiloxane.

Extrudates of the present invention can have a tubular shape. Tubular is used herein to mean a hollow, cylindrical-shaped article having an inner diameter, an inner circumference, an outer diameter and an outer circumference with a wall thickness between the outer and inner circumferences. Extrudates can have outer diameter of about 0.025 mm to about 13 mm and inner diameter of about 0.013 mm to about 12 mm. One particular example, an extrudate for a 3 mm balloon, can have a tubular shape with outer diameter of about 0.25 mm to about 2.5 mm and an inner diameter of about 0.15 mm to about 1.5 mm. The extrudates of the present invention, including, but not limited to the extrudate for the 3 mm balloon, have phase-separated microdomains that are macroscopically aligned in parallel, perpendicular, transverse, or a combination thereof. Alternatively, the extrudate can have two or more regions with different macroscopic microdomain alignment.

Extruders for use in the present invention include any extruder capable of forming tubular-shaped articles. Examples of extruders include, but are not limited to, single screw and double screw. The processing temperature depends on the actual multiblock copolymer system being used. Preferably, the temperature of extrusion is near the order-disorder transition temperature for the multiblock copolymer or the multiblock copolymer with optional solvent, additives or modifiers.

Figure 5A:
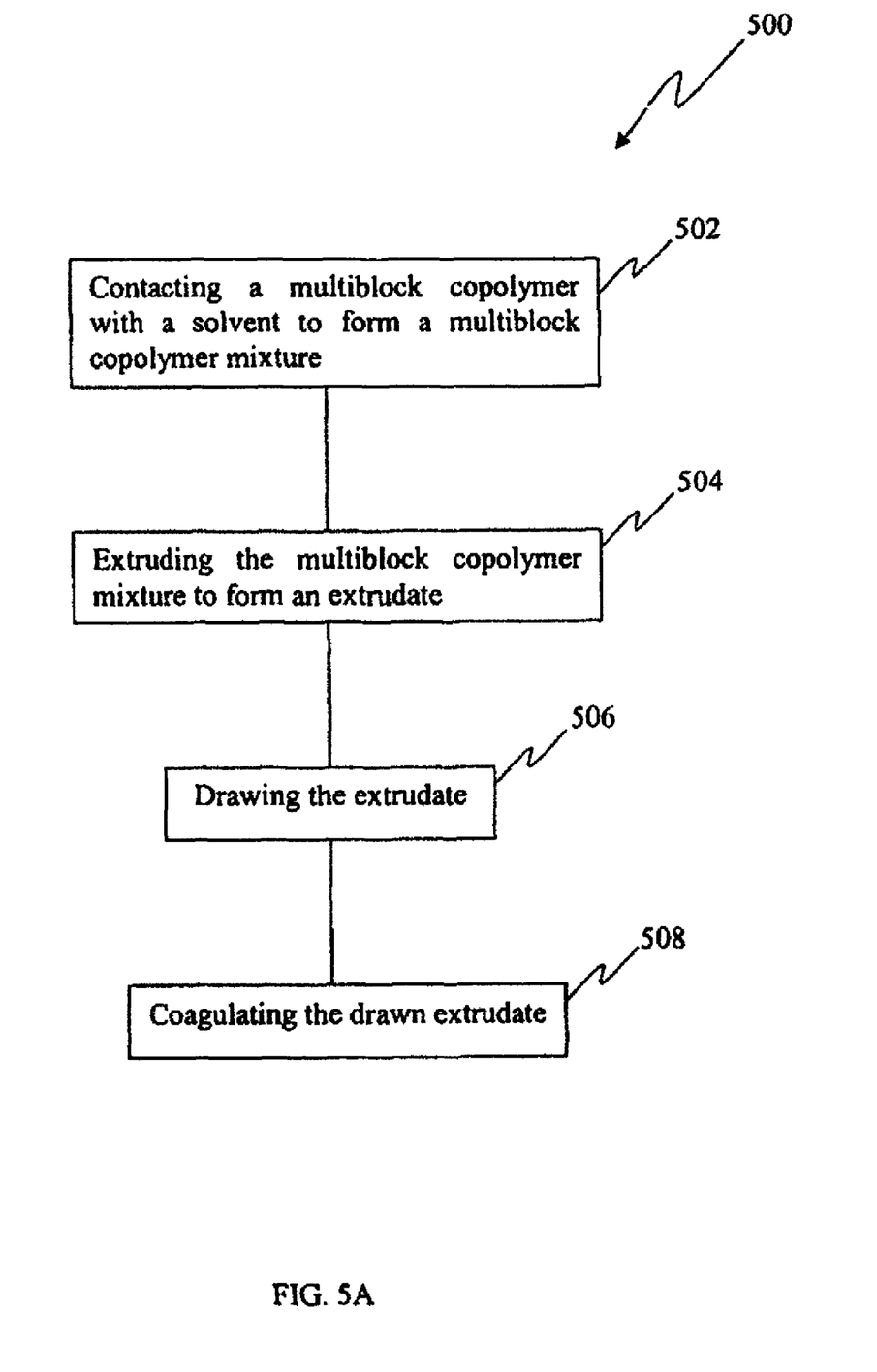
FIG. 5A is a flow diagram for a process for producing a polymeric extrudate for use as a dilatation balloon, according to an embodiment of the present invention.

In another embodiment, the present invention relates to a process for producing a polymeric extrudate for use as a dilatation balloon. In one example, FIG. 5A shows a flowchart 500 showing steps for producing a polymeric extrudate for use as a dilatation balloon. Flowchart 500 begins with step 502. In step 502, a multiblock copolymer is contacted with a solvent to form a multiblock copolymer mixture. As discussed above, the solvent can comprise a plasticizer, or alternatively, is a plasticizer. The solvent is chosen such that it reduces the entanglement of one of the phases of the multiblock copolymer. Any solvent can be used. Preferably, the solvent or plasticizer has a solubility parameter about equal to the solubility parameter of at least one of the polymer block phases. Any concentration of solvent can be used. Preferably, the concentration of solvent results in microphase separation and macroscopic ordering and alignment of the microdomains during extrusion. The resulting mixture can optionally comprise additional additives and modifiers.

Referring again to FIG. 5A, in step 504, the multiblock copolymer mixture is extruded to form an extrudate. The temperature of the extrusion process is set near the order-disorder transition temperature of the multiblock copolymer mixture, preferably just below it. The shear rate also affects the final macroscopic ordering and alignment of the microdomains. The multiblock copolymer mixture can be extruded at a constant shear rate such that the extrudate has microdomains that are macroscopically aligned parallel, perpendicular, transverse, or a combination thereof. Alternatively, the mixture is extruded at a variable rate such that the extrudate has two or more portions with different macroscopic microdomain alignment. For example, the shear rate can be set such that the molecules are aligned perpendicular to the flow, either radially outward in a starburst pattern, or in cylinders. The extrudate can optionally be cooled as it exits the extruder. Any method of cooling can be used, preferably, some fluid, for example, water, is used to cool the extrudate.

Referring again to FIG. 5A, in step 506, the extrudate is drawn. The extrudate can be drawn after exiting the extruder. Any method known to one of ordinary skill in the art can be used to draw the extrudate. Preferably, the extrudate is drawn during balloon forming. Preferably, a stretch blow-molding or a balloon forming machine is used. The extrudate can be drawn in any one direction, or in any combination of directions, for example, uniaxially or biaxially. Biaxial drawing can be performed in the longitudinal direction and the radial direction. The extrudate can be drawn to any draw ratio, including any uniaxial or any biaxial draw ratio. In biaxial drawing, the radial and longitudinal draw ratios can vary separately. The draw ratio affects the final properties of the balloon. By way of example, for approximately a 3 mm balloon, the extrudate is drawn to about 200% to 700% in the radial direction.

Referring back to FIG. 5A, in step 508, the drawn extrudate is coagulated. The extrudate is coagulated after drawing to remove solvent from the drawn extrudate. Any method known to one skilled in the relevant art can be used to coagulate the drawn extrudate. For example, a vacuum oven is used to remove the solvent. Alternatively, the drawn extrudate is coagulated in a suitable fluid. Suitable fluids include those fluids that remove the solvent from the extrudate without dissolving the extrudate, for example a $C_1$-$C_6$ alcohol.

Figure 5B:
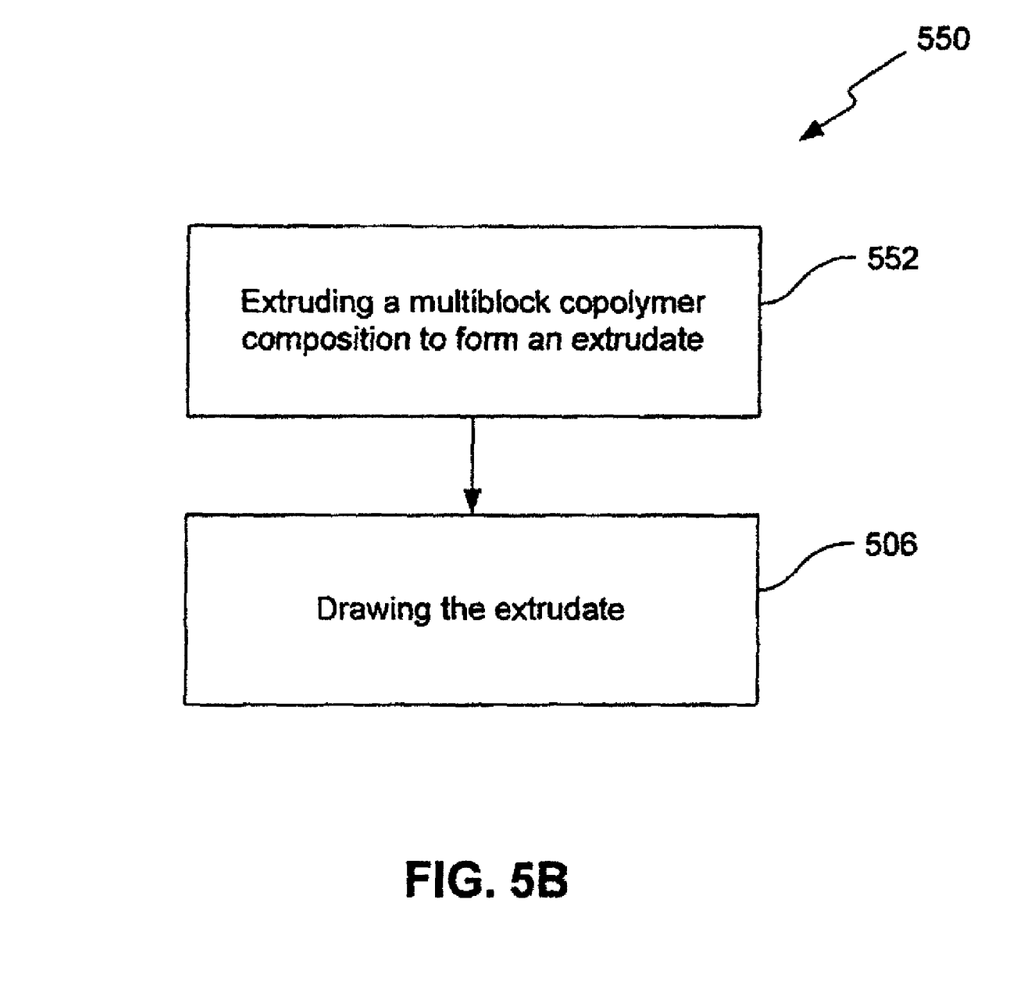
FIG. 5B is a flow diagram for an alternative process for producing a polymeric extrudate for use as a dilatation balloon, according to an embodiment of the present invention.

In another example, FIG. 5B shows flowchart 550 showing an alternative process for producing a polymeric extrudate for use as a dilatation balloon. In this example, a solventless process is used in producing the extrudate. Flowchart 550 begins with step 552. In step 552, a multiblock copolymer composition is extruded to form an extrudate. The multiblock copolymer composition comprises a multiblock copolymer. The multiblock copolymer composition can optionally further comprise other additives, modifiers or a plasticizer. As above, the temperature of extrusion is preferably set near the order-disorder transition of the composition. Also, as above, the shear rate can be constant or varied, depending on the desired final orientation of the molecules in the extrudate. Also, as above, the extrudate can be cooled as it exits the extruder. Flowchart 550 continues with step 506. In step 506, the extrudate is drawn.

An extrudate is formed having tensile strength in the range of about 50 MPa to about 450 MPa, strain at break in the range of about 50% to about 600% and elasticity at nominal strains of at least about 30%. Optionally, extrudates have substantially complete elastic recovery from nominal strains of at least about 30%. One particular, non-limiting example is a multiblock copolymer mixture is extruded to form an extrudate for making a 3 mm balloon having tensile strength in the range of about 150 MPa to about 250 MPa, strain at break in the range of about 300% to about 500% and substantially complete elastic recovery from strains of at least about 30%. An alternative example is an extrudate having tensile strength in the range of about 50 MPa to about 150 MPa, strain at break in the range of about 50% to about 300% and substantially complete elastic recovery from strains of at least about 30%. Another example is an extrudate having tensile strength in the range of about 250 MPa to about 450 MPa, strain at break in the range of about 500% to about 600% and substantially complete elastic recovery from strains of at least about 30%.

The following examples are illustrative, but not limiting, of the method and compositions of the present invention. Other suitable modifications and adaptations of the variety of conditions and parameters normally encountered in nanocrystal synthesis and which are obvious to those skilled in the art are within the spirit and scope of the invention.

Example 1

A polymeric extrudate was formed as a tubular preform for a dilatation balloon. A multiblock copolymer was used as the base material. A triblock copolymer was used having the structure (C-E-C), wherein C and E denote poly(cyclohexylethylene) (PCHE) and hydrogenated butadiene, respectively. The butadiene block is a mixture of 1-2 and 1-4 addition, which upon hydrogenation, results in a block of random poly(ethylene) (PE) and poly(ethylethylene) (PEE). The triblock copolymer is described in detail in U.S. Pat. No. 6,455,656 B2; U.S. Pat. No. 6,451,924 B1; U.S. Pat. No. 6,426,390 B1; and U.S. Pat. No. 6,376,621 B1, all of which are incorporated herein in their entireties by reference. The triblock polymer was dissolved in dioctylphthalate (DOP), where the polymer concentration was about 75 wt. %, thus creating a gel. The gel was extruded at a temperature just below the order-disorder transition temperature. The gel was subsequently drawn to 400%. The extruded and drawn samples were coagulated in a vacuum oven to extract the solvent. For Deborah numbers between 1 and 100, the macroscopic microdomain alignment was perpendicular as shown by Small Angle X-ray Scattering (SAXS) experiments and Transmission Electron Microscopy (TEM). As the Deborah number is proportional to shear rate, increasing the shear rate increases the amount of perpendicular alignment. The size of the microdomains measured about 10-20 nm. The extrudate was found to have hoop strength in excess of 150 MPa, strain at break of 120%, and complete elastic recovery after subjecting the extrudate to strains as high as 40%.

Example 2

Following a similar procedure, a pentablock copolymer was extruded having structure (C-E-C-E-C), wherein C and E denote poly(cyclo-hexylethylene) (PCHE) and hydrogenated butadiene, respectively. The butadiene block is a mixture of 1-2 and 1-4 addition, which upon hydrogenation, results in a block of random poly(ethylene) (PE) and poly(ethylethylene) (PEE). The polymer is described in U.S. Pat. No. 6,455,656 B2; U.S. Pat. No. 6,451,924 B1; U.S. Pat. No. 6,426,390 B1; and U.S. Pat. No. 6,376,621 B1. For Deborah numbers between 0.1 and 100, the macroscopic microdomain alignment was perpendicular, and a transverse alignment was also seen for Deborah numbers between 10 and 100. Similar mechanical responses were measured for the pentablock copolymer as the triblock copolymer, except the pentablock copolymer was found to have superior strength-elasticity balance as compared with the triblock extrudate.

Following a similar procedure, one can produce tubular preforms comprising a blend of 90% of the (C-E-C) triblock copolymer and 10% of the (C-E-C-E-C) pentablock copolymer.

One can attach the extrudates formed above to a catheter to form a low profile, self-wrapping dilatation catheter balloon for angioplasty applications.

Example 3

Figure 6A:
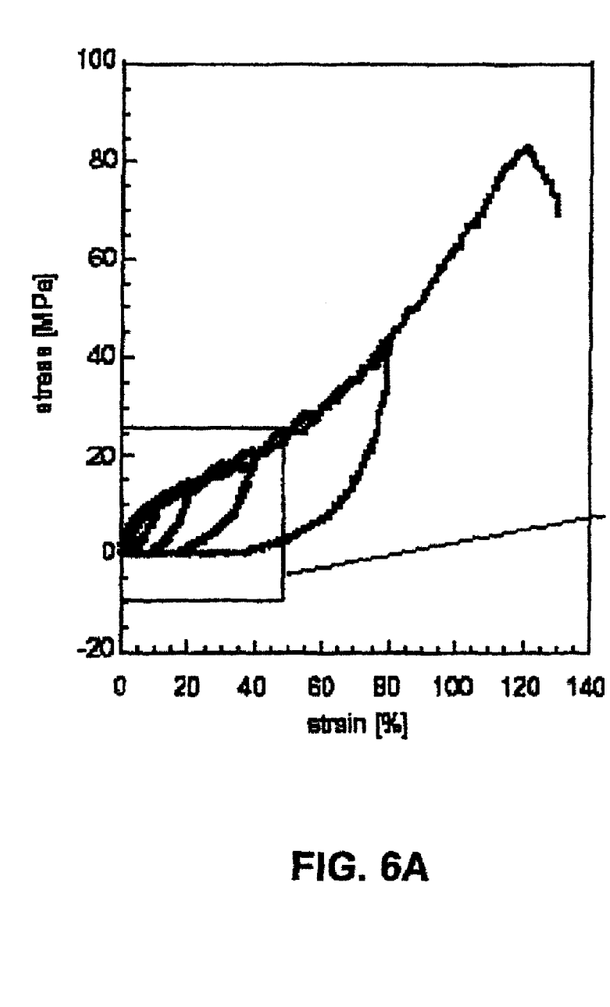
FIGS. 6A-6B show stress vs. strain curves for a multiblock copolymer extruded according to an embodiment of the present invention.
Figure 6B:
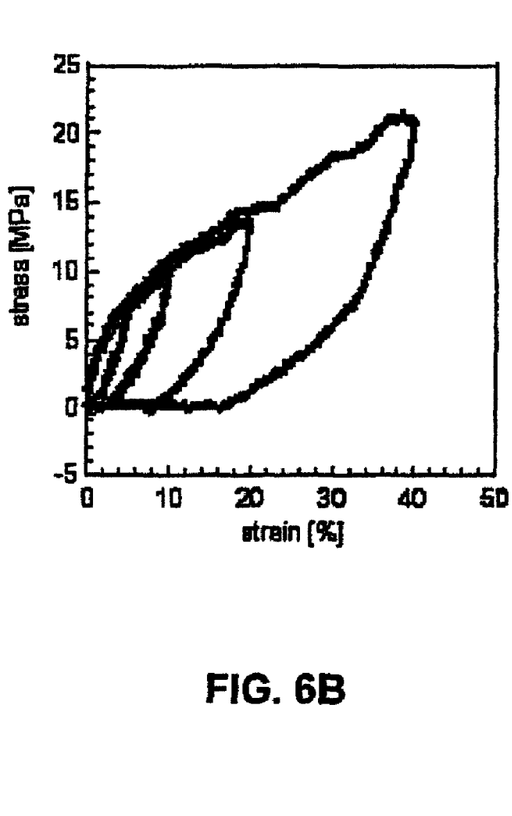

Following a similar procedure as Example 1, a pentablock copolymer having molecular weight of about 65 kg/mole and comprising about 60 wt. % of the poly(cyclohexylethylene) block and about 10 wt. % of the poly(ethylethylene) block was mixed with dioctylphthalate to form a gel having about 75 wt. % polymer. The gel was extruded and the extrudate was pre-strained or aligned by hand. The elasticity and elastic recovery of the sample was studied using a tensile machine. FIGS. 6A and 6B show the stress vs. strain (hysteresis) curves. The curves show that the material is highly elastic and substantially recovers from strains of about 4, 10, 18 and 40% without permanent deformation. FIG. 6A shows no failure of the material until strains of about 120%.

Example 4

Figure 7A:
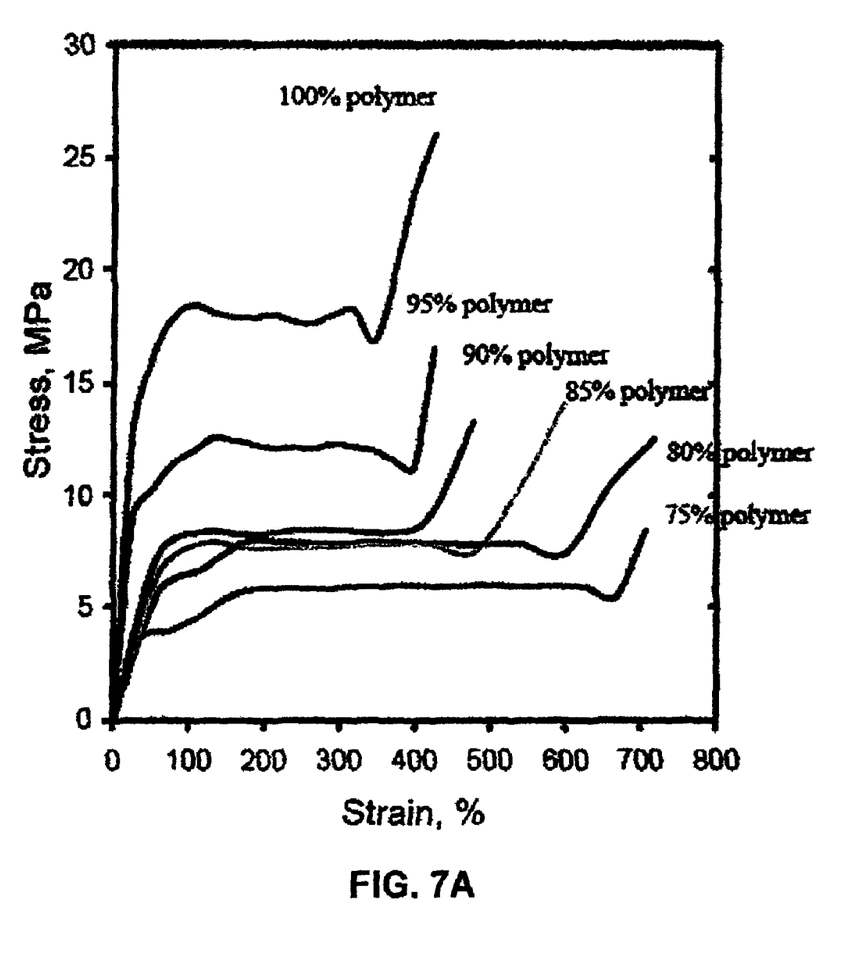
FIG. 7A shows stress vs. strain curves for extruded multiblock copolymer samples before straining, according to an embodiment of the present invention.
Figure 7B:
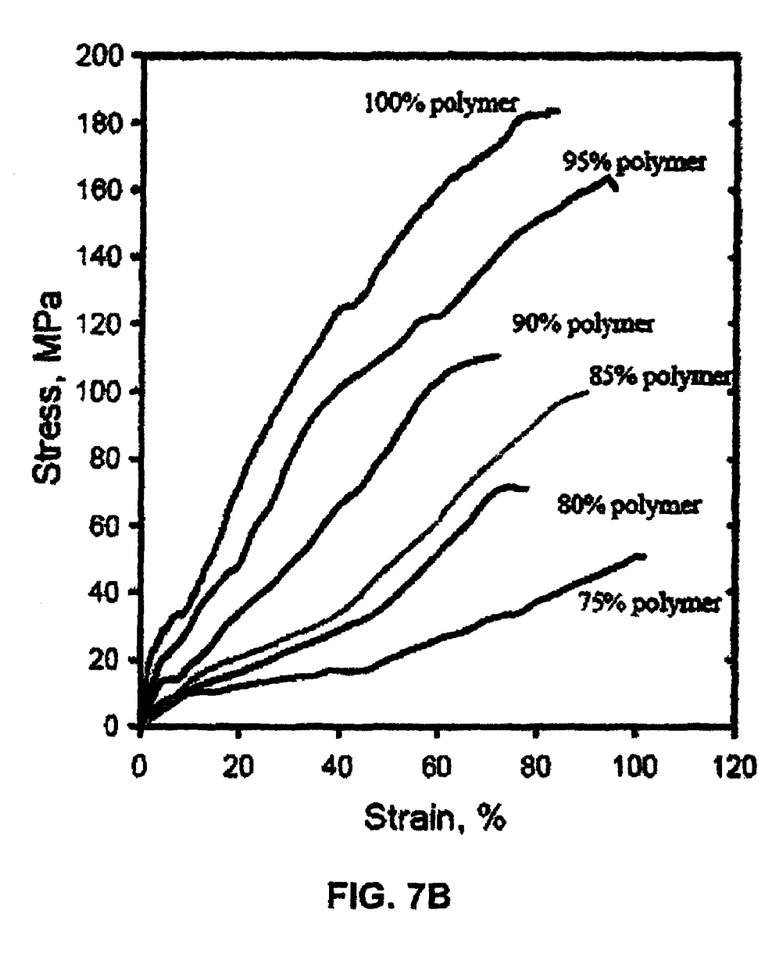
FIG. 7B shows stress vs. strain curves for extruded multiblock copolymer samples after straining, according to an embodiment of the present invention.

A series of samples were extruded comprising a pentablock copolymer and varying amounts of solvent. The pentablock copolymer had molecular weight of about 55 kg/mol and comprised about 55 wt. % poly(cyclohexylethylene) and about 10 wt. % poly(ethylethylene). Dioctylphthalate was mixed with the pentablock copolymer to form 6 samples, having 100, 95, 90, 85, 80 and 75 wt. % polymer. The samples were extruded with a capillary rheometer. The temperature of the capillary was set at about 125° C. The capillary die was about 1 mm in diameter and about 30 mm in length. A shear rate of about 11.5 $s^{-1}$ was used in the extrusion. After extrusion, the extrudate was pre-strained by hand and post-strained using an tensile machine to the completion of necking The mechanical properties of the samples were then analyzed using a tensile machine. FIG. 7A shows stress-strain curves for the six samples before straining and FIG. 7B shows stress-strain curves for the six samples after straining. The results show that the 75 wt. % gel sample had the greatest elastic response compared to the other samples.

It will be understood by those skilled in the art that various changes in form and details may be made therein without departing from the spirit and scope of the present invention as defined in the appended claims. Thus, the breadth and scope of the present invention should not be limited by any of the above-described exemplary embodiments, but should be defined only in accordance with the following claims and their equivalents.

We claim:

1. A process for producing a dilatation balloon, the process comprising:
   providing a multiblock copolymer composition comprising a multiblock copolymer, wherein the multiblock copolymer comprises glassy phase end blocks, and blocks adjacent to the end blocks comprising rubber and semi-crystalline phases; and
   forming a dilation balloon comprising extruding the multiblock copolymer composition to form an extrudate comprising phase-separated glassy, rubber, and semicrystalline microdomains that are macroscopically ordered in a perpendicular alignment;
   wherein the dilatation balloon demonstrates, during inflation, a true stress vs. nominal strain response curve comprising a first zone representative of a low modulus balloon, a second zone representative of a high strength balloon, and a sharp transition from the first zone to the second zone.

2. The process of claim 1, wherein said multiblock copolymer is a pentablock copolymer, a heptablock copolymer, or a nonablock copolymer.

3. The process of claim 1, wherein at least one block of said multiblock copolymer is polyethylene, polypropylene, poly(cylohexylethylene), polyisoprene, poly(1,3-butadiene), poly(vinyl chloride), poly(vinyl fluoride), poly(chloroprene), poly(methyl acrylate), poly(methyl methacrylate), poly(acrylonitrile), polystyrene or poly(4-vinylpyridine).

4. The process of claim 2, wherein said multiblock copolymer is a pentablock copolymer comprising poly(cyclohexylethylene) and polyethylene blocks.

5. The process of claim 1, wherein said multiblock copolymer composition further comprises an additive.

6. The process of claim 5, wherein said additive is a homopolymer.

7. The process of claim 6, wherein said homopolymer is a polydialkylsiloxane or polyethylene.

8. The process of claim 5, wherein said additive comprises at least one of a filler, antioxidant, colorant, crosslinking agent, impact strength modifier, drug or biologically active material.

9. The process of claim 1, wherein said multiblock copolymer composition further comprises a plasticizer.

10. The process of claim 9, wherein said plasticizer is a carbonamide, sulfonamide, phenolic compound, cyclic ketone, mixture of phenols and esters, sulfonated ester, sulfonated amide, N-alkylolarylsulfonamide, phthalate ester, amine, aliphatic diol or phosphite ester of an alcohol.

11. The process of claim 1, wherein said multiblock copolymer composition further comprises a solvent.

12. The process of claim 11 further including coagulating the extrudate to remove said solvent.

13. The process of claim 11, wherein the solubility parameter of said solvent and at least one block of said multiblock copolymer are about equal.

14. The process of claim 1, wherein said extruding comprises extruding at a constant shear rate.

15. The process of claim 1, wherein said dilatation balloon formed is a zero-fold balloon.

16. The process of claim 15, wherein said zero-fold dilatation balloon is self-wrapping.

17. The process of claim 1, wherein said multiblock copolymer composition is a blend of two or more multiblock copolymers.

18. The process of claim 1, wherein forming a dilation balloon further comprises drawing said extrudate.

19. The process of claim 1, wherein forming a dilation balloon further comprises stretch blow-molding said extrudate.

20. A process for producing a dilatation balloon, the process comprising:
   providing a multiblock copolymer composition comprising a multiblock copolymer, wherein the multiblock copolymer is a pentablock copolymer, a heptablock copolymer, or a nonablock copolymer, and wherein the multiblock copolymer comprises glassy phase end blocks, and blocks adjacent to the end blocks comprising rubber and semi-crystalline phases; and
   forming a dilatation balloon comprising extruding the multiblock copolymer composition at a constant shear rate to form an extrudate comprising phase-separated glassy, rubber, and semi-crystalline microdomains that are macroscopically ordered in a perpendicular alignment;
   wherein the dilatation balloon, during inflation, demonstrates a true stress vs. nominal strain response curve comprising a first zone representative of a low modulus balloon, a second zone representative of a high strength balloon, and a sharp transition from the first zone to the second zone.

21. The process of claim 20, wherein forming a dilation balloon further comprises drawing said extrudate.

22. The process of claim 20, wherein forming a dilation balloon further comprises stretch blow-molding said extrudate.

23. A process for producing a dilatation balloon, the process comprising:
   providing a multiblock copolymer composition comprising a pentablock copolymer, wherein the pentablock copolymer comprises glassy phase end blocks, and blocks adjacent to the end blocks comprising rubber and semi-crystalline phases; and
   forming a dilatation balloon comprising:
      extruding the multiblock copolymer composition at a constant shear rate to form an extrudate comprising phase-separated glassy, rubber, and semi-crystalline microdomains that are macroscopically ordered in a perpendicular alignment; and
      drawing said extrudate,
   wherein the dilatation balloon, during inflation, demonstrates a true stress vs. nominal strain response curve comprising a first zone representative of a low modulus balloon, a second zone representative of a high strength balloon, and a sharp transition from the first zone to the second zone.

* * * * *